(12) United States Patent
Wolff

(10) Patent No.: US 11,957,786 B2
(45) Date of Patent: Apr. 16, 2024

(54) LIQUID VAPE BASE AND EXTRACTION PROCESS

(71) Applicant: Therapur Tech, LLC, Wilmington, DE (US)

(72) Inventor: Francis Wolff, Miami, FL (US)

(73) Assignee: TPRX Tech, LLC, Wilmington, DE (US)

( * ) Notice: Subject to any disclaimer, the term of this patent is extended or adjusted under 35 U.S.C. 154(b) by 676 days.

(21) Appl. No.: 16/274,081

(22) Filed: Feb. 12, 2019

(65) Prior Publication Data

US 2019/0247297 A1    Aug. 15, 2019

Related U.S. Application Data

(60) Provisional application No. 62/630,487, filed on Feb. 14, 2018, provisional application No. 62/629,453, filed on Feb. 12, 2018.

(51) Int. Cl.

| | | |
|---|---|---|
| *A61K 9/00* | (2006.01) |
| *A61K 31/05* | (2006.01) |
| *A61K 31/353* | (2006.01) |
| *A61K 31/465* | (2006.01) |
| *A61K 36/23* | (2006.01) |
| *A61K 36/38* | (2006.01) |
| *A61K 36/484* | (2006.01) |
| *A61K 36/53* | (2006.01) |
| *A61K 36/77* | (2006.01) |
| *A61K 36/81* | (2006.01) |
| *A61K 36/88* | (2006.01) |
| *A61K 47/10* | (2017.01) |
| *A61K 47/46* | (2006.01) |

(52) U.S. Cl.
CPC .............. *A61K 9/007* (2013.01); *A61K 31/05* (2013.01); *A61K 31/353* (2013.01); *A61K 31/465* (2013.01); *A61K 36/23* (2013.01); *A61K 36/38* (2013.01); *A61K 36/484* (2013.01); *A61K 36/53* (2013.01); *A61K 36/77* (2013.01); *A61K 36/81* (2013.01); *A61K 36/88* (2013.01); *A61K 47/10* (2013.01); *A61K 47/46* (2013.01)

(58) Field of Classification Search
None
See application file for complete search history.

(56) References Cited

U.S. PATENT DOCUMENTS

| | | | | |
|---|---|---|---|---|
| 2014/0144429 A1* | 5/2014 | Wensley | ............... | A61M 15/06 128/200.14 |
| 2016/0174603 A1 | 6/2016 | Abayarathna et al. | | |
| 2016/0262443 A1 | 9/2016 | Piccirilli et al. | | |

FOREIGN PATENT DOCUMENTS

| | | | | |
|---|---|---|---|---|
| CN | 101919584 A | 12/2010 | | |
| CN | 104585870 A | 5/2015 | | |
| CN | 104585870 B | 8/2016 | | |
| IT | MI20131138 A1 * | 1/2015 | ........... | A24F 47/008 |
| IT | MI20131138 A1 | 1/2015 | | |
| WO | 2014125340 A1 | 8/2014 | | |
| WO | WO-2014125340 A1 * | 8/2014 | ........... | A61K 31/465 |

OTHER PUBLICATIONS

Hahn et al. Tobacco Induced Diseases (2014) 12:23. 12 pages. (Year: 2014).*
International Search Report & Written Opinion, for Application No. PCT/US2019/017716, dated May 27, 2019.
Direction to request examination for patent application, dated Nov. 15, 2022, issued in related AU Application No. 2019218399.
Search Report issued in European Patent Application No. 19751397.1 dated Dec. 21, 2021.

* cited by examiner

*Primary Examiner* — Michael V Meller
(74) *Attorney, Agent, or Firm* — Davis Graham & Stubbs LLP

(57) ABSTRACT

A botanical matrix and a base are disclosed for use in producing vapes. The base includes propanediol, vegetal glycerin and a blend of two or more botanical additives. The propanediol and glycerin may be lab produced for improved consistency. Additional ingredients including active ingredients may be added to the base to produce a vape. The botanical additives provide a base that has a smoother impression and reduces or eliminates throat burn.

18 Claims, 1 Drawing Sheet

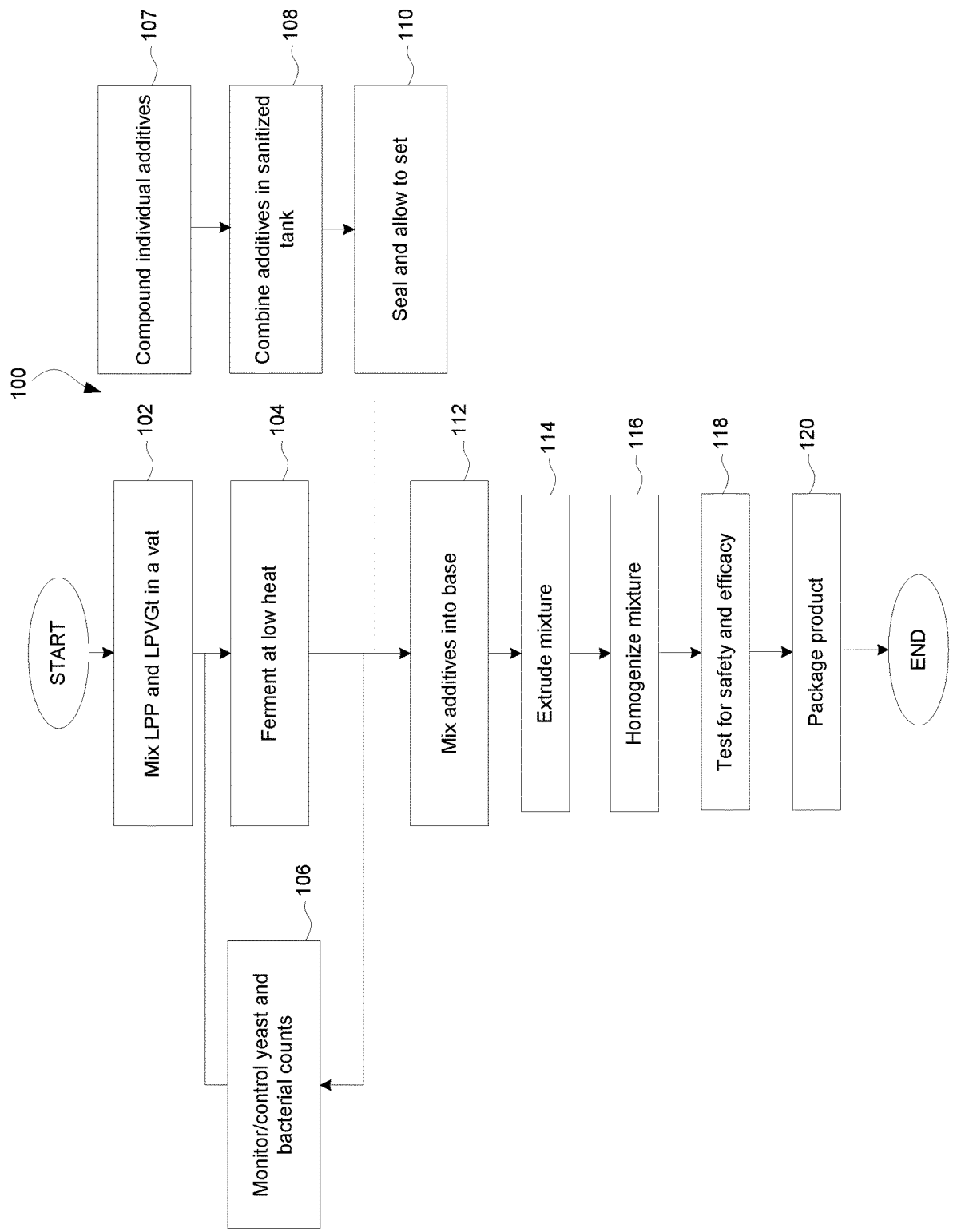

LIQUID VAPE BASE AND EXTRACTION PROCESS

CROSS-REFERENCE TO RELATED APPLICATION

This application claims priority from U.S. Provisional Application No. 62/630,487, entitled, "Liquid Vape Base and Extraction Process," filed on Feb. 14, 2018 and claims priority from U.S. Provisional Application No. 62/629,453, entitled, "Liquid Vape Base and Extraction Process," filed on Feb. 12, 2018. The content of the above-noted applications are incorporated herein by reference as if set forth in full and priority to this application is claimed to the full extent allowable under U.S. law and regulations.

FIELD OF THE INVENTION

The present invention relates generally to compositions of matter, methods for extraction and production and the products resulting therefrom, all associated with vaping solutions for inhalation and bases for generating the vaping solutions.

BACKGROUND

In recent years, the practice of "vaping" has been growing. Generally, vaping is the process of atomizing a solution and inhaling the resulting vapors. A solution may include a liquid product (e.g., base), that may include certain additives, which serves as a carrier for a variety of active ingredients which are added to the base to form a vaping solution. When the solution is atomized, tiny droplets of solution are formed, each containing base and active ingredients. In this regard, the base may carry the active ingredients for delivery to a user's lungs.

Conventional vaping solutions thus comprise a base (including additives) and active ingredients. The base includes the liquids that form the bulk of the solution. The additives may include flavorings and other ingredients that enhance the vaping experience. The active ingredients are the ingredients that provide the desired vaping effect such as psychoactive effects, delivery of medicine and delivery of healthful agents or recreational products, among others.

There are any number of uses and motivations for vaping. For example, smokers frequently turn to vaping as an alternative to cigarettes. In this regard, nicotine may be one of several active ingredients added to a base and delivered into the bloodstream through inhalation of the vaping solution into the lungs. Many other agents may be delivered in this manner and other components, such as flavorings, may be added.

One common method of vaping involves the use of an electronic cigarette ("e-cigarette"). Many e-cigarettes include a heating element which converts the solution into a vapor. Additionally or alternatively, some e-cigarettes utilize a piezoelectric diaphragm for the atomization. In either instance, the design of an e-cigarette is generally intended to maintain the solution and vapors at a temperature below ignition. In this regard, it is often believed that vaping is healthier than smoking cigarettes at least because there are no burned substances entering the lungs.

One common practice in the vaping industry has been to create a base with petroleum-based propylene glycol (PG) or polyethylene glycol (PEG) (together, "glycol"). Glycol is a consistent and stable carrier for additives and active ingredients that allows specific dosing when subjected to extreme heat. However, glycol is considered by many to be an undesirable product for ingestion because it is a synthetic, rather than natural, product and because of connotations associated with its common industrial applications (e.g., production of polyester resins and polyurethanes, aircraft deicing). Additionally, some believe certain glycols to be carcinogenic and many users of e-cigarettes report undesirable side effects from glycol bases such as throat irritation.

For at least the reasons above, there is a need in the vaping industry for a natural alternative to harsh, synthetic glycol vaping bases.

SUMMARY OF THE INVENTION

The present invention includes subject matter (e.g., methods, compositions, products-by-processes etc.) related to a liquid base useful for vaping that comprises entirely or substantially entirely naturally occurring substances. In some cases, such naturally occurring substances may be replicated in the laboratory for improved process control, but substances that do not occur in nature are avoided to the maximum extent possible. The products can be produced using renewable plant-based materials free from preservatives or synthetic chemicals, and can be sourced so that the ingredients are traceable from farm to final product.

It is an objective of the present invention to provide a base having a smoother impression that reduces or eliminates throat burn. It is believed that such a base may be healthier for a user's respiratory system and may act to detoxify and even heal the lungs while providing a carrier or delivery system for additional ingredients including active ingredients (e.g., extracts, compositions, and flavorings). The intended uses of embodiments of the invention may cover, inter alia, nicotine e-cigarettes, tobacco, THC vaping, bronchial inhalers, medications, vitamins, and dietary supplements. While much of the description below makes use of specific examples in discussing various aspects of the invention, such examples are intended merely for illustrative purposes and the invention is not limited to any specific operational characteristics disclosed herein.

The discussion below includes descriptions of various products including bases and vapes. Each of these, in turn, involves multiple ingredients in many cases. To avoid confusion, certain conventions are generally followed below concerning terminology. In particular, certain "bases" are described below that include two primary components that form the bulk of the bases and certain "additives" that impart certain desired qualities to the bases. Such bases are sometimes referred to as carriers or thinners according to their use, and the "bases" of the present invention are intended to encompass such products regardless of the label. A "vape" is produced by adding "additional ingredients" to the base. The additional ingredients may include "active ingredients" to produce the desired vaping effect and other ingredients such as flavorings or the like. In some cases, a particular component may be an additive or an additional ingredient depending on how it is used. Manufacturers may consider interactions or other cumulative effects associated with the combinations of additives and additional ingredients in a vape to avoid harmful effects and to optimize dosing and desired effects.

In accordance with one aspect of the present invention, a composition is provided for use in producing a vaping product. That is, the composition may be added to other components to yield a base or a vape. The composition includes at least two botanicals from the group consisting of *lobelia*, coltsfoot, *eucalyptus*, lungwort, oregano, and algae. Each of these botanicals has been found to provide benefits related to improved throat feel and healing of the respiratory tract when inhaled in a vaping product. In particular, as the botanicals each provide unique and complementary benefits, combinations of two or more of these botanicals are believed to be particularly beneficial. For example, different ones of these botanicals may be combined so as to yield effects associated with an expectorant, an antitussive, an anti-inflammatory, an astringent, a tonic, an antioxidant, a humectant, or any desired combination and weighting of the desired effects. A combination of all of the noted botanicals is believed to be particularly beneficial, but it is anticipated that excellent products may be produced while eliminating one of the botanicals (i.e., using the other five) as may be desired to avoid any potential interaction, effect or supply difficulty.

The noted botanicals may be added to various bases or combinations of base components to yield an improved base. Particular combinations of base components are described below, but others may be used in accordance with the present invention. The botanicals may provide benefits even when used in connection with conventional bases noted above. Similarly, a medium chain triglyceride (MCT) or other base may be used in place of the bases described below or in place of a component thereof, may be used with modified formulations of the botanicals to form a base, or may be used as a base or base components with specific vape formulations described below or modified versions thereof (e.g., the account for interactions specific to MCT). Such MCT formulations may be specifically used in low temperature vaping implementations (e.g., at temperatures not exceeding 200° C.).

In accordance with another aspect of the present invention, a base is provided for use in manufacturing a vape. The base includes propanediol, a glycerin such as vegetal glycerin (VGt) and a blend of two or more botanical additives. The propanediol and VGt may be lab produced for improved consistency. The botanicals may be, for example, selected from the group *lobelia*, coltsfoot, *eucalyptus*, lungwort, oregano, and algae juice as discussed above. In one implementation, all of the noted botanical additives may be used. It is been found that the botanical additives provide a base that has a smoother impression and reduces or eliminates throat burn.

In accordance with a still further aspect of the present invention, a vape is provided that includes a base and one or more active ingredients for producing a desired physiological effect. The base may comprise ingredients as described above including the botanical additives. The active ingredients may include an ingredient selected from cannabidiol, tetrahydrocannabinol, nicotine, guarana, caffeine, a dietary supplement, a vitamin, and medication. Additional ingredients such as flavorings may be included.

According to a still further aspect of the present invention, a method is provided for use in producing a vaping product such as a base and/or a vape. The method includes blending propanediol and VGt to form a mixture, blending a plurality of additives into the mixture, and mixing the additives into the mixture to form a base. The mixture may be maintained at a temperature of, for example, between about 90° F.-120° F. during this process. The base may then be used to form a vape. In this regard, an active ingredient may be blended with the base to form the vape. The active ingredient may be selected from the group cannabidiol, tetrahydrocannabinol, nicotine, guarana, caffeine, a dietary supplement, a vitamin, and medication. The invention further includes products produced by the noted processes.

In accordance with a still further aspect of the present invention, a vape is provided. The vape comprises a base and active components including at least two ingredients selected from the group holy basil, saffron, ashwagandaha, licorice, gotu kola, and Saint John's wort. These ingredients, in various combinations, have been found to provide enhanced energy when inhaled in a vape. Certain formulations include five of these ingredients (an energy vape omits Saint John's wort and a sustained energy vape excludes gotu kola).

Additional details of the base, vapes, specific formulations, production processes and further advantages of the invention are set forth in the description below.

BRIEF DESCRIPTION OF THE DRAWING

For a more complete understanding of the present invention, and further advantages thereof, reference is now made to the following detailed description, taken in conjunction with the drawing, in which:

FIG. 1 is a flowchart illustrating a process for producing a vaping product in accordance with the present invention.

DETAILED DESCRIPTION

The present invention is based in part on the desire to create an improved product that would not flash or ignite at high temperatures found in atomizers of some vape devices. In that regard, an initial objective was to find natural plants, herbs and/or botanicals that could be combined with a vegetal or vegetable glycerin (VGt) to form a substitute for glycols. The botanicals oxygenate the smoking process to reduce throat irritation while remaining non-toxic even at the flash points of the various ingredients. The invention also provides base liquids and additives that are not prone to ignite at temperatures found in atomizers as ignition may lead to free radicals, oxidation, tar, and lacquering, thereby leaving residue and harmful substances in the lungs.

A replacement for propylene glycol has been developed that is made from natural ingredients that may effectively deliver the desired additive(s). In one implementation, this liquid base is naturally derived from traditional corn-based propanediol which is made by fermenting corn. Although the propanediol is thus made from natural ingredients, it may be laboratory produced for consistency and optimized properties. Laboratory-produced propanediol has been found to provide favorable boiling points, melting points, and densities compared to other propanediols.

Furthermore, the laboratory-produced propanediol ("LPP") mixes well with a laboratory-produced vegetable glycerin resulting in reduced toxicity liquid base that will stay in stable composition with the additives (e.g., botanical elements). There are a variety of vegetal glycerin blends which may be suitable for the present invention. In one embodiment, a vegetal glycerin derived from steam distillation of corn seeds, leaves, or husks is blended with a triglyceride mixture distilled from coconut, soy, and bamboo to yield VGt. Again, although the VGt is thus made from natural ingredients, it may be laboratory produced for consistency and optimized properties, thus yielding a laboratory-produced vegetable glycerin ("LPVGt"). Suitable propanediol and glycerin products that are not laboratory produced are available in the marketplace. These products include 1.3-Propanediol (e.g., Du Pont® Zemea®) and Vegetable Glycerin USP 99%. Exemplary bases may include about 45-55% LPP and about 45-50% LPVGt as described below.

In order to combat throat and lung irritation, it may be desirable to use herbal or botanical additives which may soothe and heal the irritated mucous linings of the respiratory system. In this regard, burn tests have been performed on a number of herbal and botanical substances. The tests were monitored for a measure of oxygenation at the boiling point of the liquid base. Those that would not ignite at the boiling point of the liquid base were selected as they may reduce aggravation in the throat and lungs and may even offer antioxidant properties. These additives include humectants, expectorants, and anti-oxidants.

Volatile oils may be extracted from herbal and botanical substances ("botanicals") for use as additives. Various processes may be utilized for extraction including, but not limited to, liquid extraction, steam distillation, centrifugal processing, extrusion, and/or oxygen micronization. The order of processing steps and enhancements to be performed on certain extractions may be altered to affect characteristics of the base. An extraction process may be selected for each particular botanical with the objective of yielding the most pure and desirable result for that particular botanical.

In this regard, it is noted that different botanical suppliers may provide botanicals in varying degrees of readiness for extraction, which may require a slightly different extraction process. For example, a centrifuge may be used with certain ingredients to eliminate any small particles from the final extraction. In addition, oxygenation and homogenization, in connection with a mesh may be employed to ensure a well-concentrated homogenous blend that will not separate over time. The use of a liquid extraction or a steam extraction is based upon the specific plant, however, for a manufacturing process liquid-liquid extraction could generally be used if consistent botanicals are supplied. Algae typically involves a separate approach. It is used in its whole form and is first dehydrated to concentrate the micro-nutrients. Then they are re-hydrated with purified water and then micronized and oxygenated during the homogenization process to create the extract or "juice."

Additives used in conjunction with a base may include, inter alia, *lobelia*, coltsfoot, *eucalyptus*, lungwort, oregano, and algae juice. These botanicals can be tracked from their origins to production to ensure quality and purity. The above-the-ground parts of the *lobelia* plant (*Lobelia inflata*) are used, among other things, because they contain chemicals that thin mucous to aid expectoration. The leaves of the coltsfoot plant (*Tussilago farfara*) are used at least to make medicines that help with lung problems such as bronchitis by reducing swelling and inflammation. The dried leaves and oil of the *eucalyptus* tree (*Eucalyptus globulus*) are known to loosen coughs and to treat respiratory tract infections and reduce the swelling of the mucous membranes of the respiratory tract. The aerial parts of the lungwort plant (*Pulmonaria officinalis*) are known to treat breathing conditions and are often used in cough medicines. The leaves of the oregano plant (*Origanum vulgare*) are known to reduce coughs and spasms, and possess antioxidant properties. Algae, in its many forms, is incorporated as a juice because of its antioxidant and humectant properties. The combination of the listed botanicals creates a comprehensive, 100% natural, vaping base to reduce throat burn by simultaneously soothing and healing the respiratory tract. The botanical matrix provides beneficial moisture to oral tissues, reduces inflammation, and delivers tonic properties and antioxidants to allow a more enjoyable vaping experience. It will be appreciated that the effects noted above for the various additives are provided by way of example and the additives may have additional effects, both known and unknown. These additives and certain of their effects are summarized in the table below.

Botanic Matrix

| Common Name | Latin Name | Plant Parts | Extraction | Property | Use |
|---|---|---|---|---|---|
| *Lobelia* | *Lobelia inflata* | Above ground parts | Liquid extraction & centrifuge; micronization w/oxygen | Expectorant | For upper respiratory complaints, and in cough medicines to thin mucus to make it easier to expectorate and enable breathing |
| Coltsfoot | *Tussilago farfara* | Leaves | Steam distillation | Antitussive; expectorant, and anti-inflammatory | Reduces pain, swelling, and inflammation in the respiratory tract |
| Eucalyptus (Cineole) | *Eucalyptus globulus* | Leaves | Steam distillation | Expectorant | Helps to loosen coughs and reduce swelling |
| Lungwort | *Pulmonaria officinalis* | Aerial parts | Liquid extraction & centrifuge | Astringent; expectorant | Used to treat lung diseases and isused in cough medicine or to treat breathing conditions |
| Oregano | *Origanum vulgare* | Leaves | Liquid extraction, centrifuge, and homogenization | Expectorant; tonic, antioxidant | Used to treat respiratory tract disorders and coughs |
| Algae | Brown alga | Whole plant | Micronized oxygen matrix | Antioxidant; humectant | Works to detoxify and prevent damage to the body; reduce inflammation and support the immune system |

It will thus be appreciated that different combinations of these additives may be used in differing amounts depending on the effects that are desired. In this regard, the percentages listed herein are for the base of the vaping solution, including the additives but excluding the active ingredients (which will be delivered in amounts sufficient to achieve the desired vaping effect by one or more vaping events). It will be appreciated that the relative amount of LPP/LPVGt mixture may be increased (or not) depending on the number of additives involved and may comprise 91-99% and, more preferably, about 93-97% of the base. The combination of additives that form a botanical matrix may comprise 1-9% and, more preferably, about 3-7% of the base. The best results, in terms of reduced irritation and improved healing of the respiratory tract have been achieved by combinations of multiple additives each having a preventive or healing respiratory effect such as an expectorant, an antitussive, a humectant, an antioxidant, an astringent and/or an anti-inflammatory.

Thus, various amounts and combinations of these additives may be used. For example, a solution may comprise 1-10% *lobelia* (more preferably, between about 1-3%), 0.5-5% coltsfoot (more preferably, between about 0.5-2%), 0.5-5% *eucalyptus* (more preferably, between about 0.5-2%), 0.25-2.5% lungwort (more preferably, between about 0.25-1%), 0.25-2.5% oregano (more preferably, between about 0.25-1%), and 0.1-2.5% algae juice (more preferably, between about 0.1-0.5%). In one embodiment, a solution may comprise about 2% *lobelia,* 1% coltsfoot, 1% *eucalyptus,* 0.5% lungwort, 0.5% oregano, and 0.25% algae juice, by weight or by volume.

Any appropriate means of extraction of the various additives may be utilized. In one implementation, *lobelia* may comprise a lobeline extrusion processed liquid extraction and a centrifuge and micronization with oxygen; coltsfoot may be extracted with steam distillation; *eucalyptus* may be extracted from cineole with steam distillation; lungwort may be extruded to extract volatile juice and oil or liquid extraction; oregano may be extruded or extracted by liquid extraction and homogenized, and algae juice may be micronized with oxygen, e.g., to act as a humectant and keep lungs moist. Additionally or alternatively, some ingredients may be encapsulated using standard laboratory processes. Encapsulation may discourage tampering with the formulation or reverse-engineering. Trace elements and minerals may also be employed in the additives to make them clinically relevant to batch compounding.

In one aspect, the present invention includes the additives and the way they are compounded. All of the ingredients (e.g., liquid base and additives) may be cool-compounded into solution by screwing at a temperature below 180° F., more preferably at a temperature between about 145-160° F., for example, 152° F. It is believed that temperatures above 180° F. may undesirably cook the ingredients.

Any appropriate production process may be utilized. The following is a description of one implementation of a therapeutic formulation produced by a production process (100), and is provided for exemplary purposes, with reference to the flowchart of FIG. 1:

The illustrated process is initiated by creating a base by mixing (102) 48.7% propanediol (e.g., LPP) and 46% vegetal glycerin (e.g., LPVGt) in a vat with a scraper, and fermenting (104) at 106° F. for approximately three hours or until the mixture loses it milky white appearance (e.g., may become translucent). This mixture induces a fermentation process. The laboratory fermentation process includes the use of yeast in a first phase of the process, and then a bacterial culture in a second phase. At completion, solids are filtered out of the liquid by using a 50-60 micron filtration screen. Accordingly, it may be desirable to monitor and control (106) yeast and bacterial counts to be congruent with lab standards for traditional fermentation. The resulting mixture is then homogenized. Separately, the additives (e.g., botanical and herbal ingredients such as *lobelia*, coltsfoot, *eucalyptus*, lungwort, oregano and algae juice) are compounded (107) and combined (108) in a sanitized tank. This blend of ingredients should be pre-measured, compounded, sealed and allowed to set (110) for approximately 12 hours at room temperature. The entire matrix is then run through homogenization (which helps bind oxygen) for 10 minutes.

The process then proceeds with the following steps:

The additives are mixed (112) into the base. The finished matrix may be slowly poured from the tank into the base. Light extrusion screwing (114) may be utilized for 5-6 hours or until no separation occurs.

The matrix is then homogenized (116) for about 10-30 minutes or until fully oxygenized and the solution is fully integrated with no sign of separation.

The resulting product can then be tested (118) for appropriate safety and efficacy.

Finally, the product is promptly poured into drums or any appropriate packaging (120) that can be medically sealed.

A specific example of a base according to the present invention includes the following ingredients:
1. 48.75% bio (corn)-based 1,3-Propanediol or LPP
2. 46.00% Vegetable Glycerin USP 99% or LPVGt
3. 02.00% *Lobelia inflate* (*Lobelia*) Extract and Centrifuge
4. 01.00% *Tussilago farfara* (Coltsfoot) Steam distillation and Centrifuge
5. 01.00% *Eucalyptus globulus*/horistes (*Eucalyptus*) Steam distillation
6. 00.50% *Pulmonaria officinalis* (Lungwort) Extract, Juice and Volatile oil
7. 00.50% *Origanum vulgare* (Oregano) Extract, Homogenized
8. 00.25% Viridiplantae chlorophyta (Algae) Algae Juice Micronized and Oxygen Matrix The ingredients may be processed as described above to yield a base in accordance with the present invention.

The resulting solution is believed to be a safe and effective carrier for additional ingredients including active ingredients which may be added alternatively or additionally to the described additives to yield a vape. For example, CBD, THC, marijuana, tobacco, nicotine, guarana/caffeine, dietary supplements, vitamins, and medications or combinations thereof may be employed as active ingredients depending on the desired effect.

The described formulation may be modulated to generate more or less steam vapor by altering the ratio of LPVGt to LPP. Furthermore, embodiments of the described composition of matter may be flavored.

In the examples of vapes described below, the base may be, in each case, formulated and processed as described above. However, it will be appreciated that manufacturers may perform research and testing concerning interactions or other combined effects as between the base additives and the additional ingredients used to generate the vape. Accordingly, the bases used for forming the vapes below may include a full set of additives as described above, or at least a subset of such additives, but it is possible that certain vapes may eliminate all of the additives.

A specific example, a herbal mix is added to the base to produce an "energy vape." The herbal mix includes:
1. Holy basil—*Ocimum tenuiflorum*
2. Saffron—*Crocus sativus*
3. Ashwagandaha root—*Withania somnifera*
4. Licorice root—*Glycyrrhiza glabra*
5. Gotu kola (Brahmi) leaf—*Centella asiatica* or,
6. Saint John's wort—*Hypericum perforatum*, in an alternate sustained energy version In one variation, both a regular energy vape and a sustained energy vape are provided. The botanic matrices of these energy vapes are further described in the tables below:

TPRX "Regular Energy Vape" Botanic Matrix

| Common Name | Latin Name | Plant Parts | Extraction | Property | Use |
|---|---|---|---|---|---|
| Holy basil | *Ocimum tenuiflorum* | Leaves and aerial parts | Steam distillation | Adaptogen; antioxidant | Anti-inflammatory |
| Saffron | *Crocus sativus* | Dried stigmata | Steam distillation | Anti-depressant | Mood elevation |
| Ashwagandaha | *Withania somnifera* | Root and berry | Liquid - liquid extraction | Adaptogen (Indian ginseng); tonic | Anti-inflammatory; stress reduction; immune system stimulant |
| Licorice | *Glycyrrhiza glabra* | Root | Liquid - liquid extraction | Adaptogen | Anti-inflammatory; stress reduction |
| Gotu kola | *Centella asiatica* | Leaves; above-ground parts | Steam distillation | Adaptogen | Anti-inflammatory |

TPRX "Sustained Energy Vape" Botanic Matrix

| Common Name | Latin Name | Plant Parts | Extraction | Property | Use |
|---|---|---|---|---|---|
| Holy basil | *Ocimum tenuiflorum* | Leaves and aerial parts | Steam distillation | Adaptogen; antioxidant | Anti-inflammatory |
| Saffron | *Crocus sativus* | Dried stigmata | Steam distillation | Antidepressant | Mood elevation |
| Ashwagandaha | *Withania somnifera* | Root and berry | Liquid - liquid extraction | Adaptogen (Indian ginseng); tonic | Anti-inflammatory; stress reduction; immune system stimulant |
| Licorice | *Glycyrrhiza glabra* | Root | Liquid - liquid extraction | Adaptogen | Anti-inflammatory; stress reduction |
| Saint John's wort | *Hypericum perforatum* | Above-ground parts | Steam distillation | Antidepressant | Mood regulation |

Each ingredient in this formulation is used in substantially equal amounts to provide the total formula, and it is prepared in a manner similar to therapeutic botanical formulation described above, with liquid extraction, and combined as a concentrate that would be poured into the LPP-LPVGt base on top of the therapeutic botanical matrix discussed above. Any additional ingredients such as THC, CBD, nicotine or a flavoring would be added and "lightly mixed" during the original 5-6 hours, and again homogenized until full oxygenized. Again, potential interactions and other combinative effects may be considered in relation to the base additives and vape ingredients, or any other combination of components. In particular, some researchers have noted potential concerns or interactions related to gotu kola and Saint John's wort. Thus, it is anticipated that these may be eliminated from the formulations noted above or other ingredients may be added or substituted.

While this specification contains many specifics, these should not be construed as limitations on the scope of the disclosure or of what may be claimed, but rather as descriptions of features specific to particular embodiments of the disclosure. Furthermore, certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The above described embodiments including the preferred embodiment and the best mode of the invention known at the time of filing are given by illustrative examples only.

What is claimed:

1. A vaping cartridge, comprising:
    a base including:
        a mixture of propanediol and vegetal glycerin (VGt) derived form at least one of corn, coconut, soy, and bamboo, said mixture comprising between 91-99% of said base by weight; and
        a blend of botanicals including *lobelia* comprising between about 1-3% of said base by weight, coltsfoot comprising 0.5-2.0% of said base by weight, algae juice comprising 0.1-2.5% of said base by weight; and
    one or more active ingredients, separate from the blend of botanicals, for producing a desired physiological effect.

2. The mixture of claim 1, wherein the propanediol comprises a laboratory produced propanediol (LPP).

3. The mixture of claim 1, wherein the VGt comprises a laboratory produced vegetal glycerin (LPVGt).

4. The mixture of claim 1, wherein the blend of botanicals comprises at least two additional botanicals selected from eucalyptus, lungwort and oregano.

5. The mixture of claim 1, wherein said base comprises from about 5% to about 95% propanediol by weight.

6. The mixture of claim 1, wherein said base comprises from about 5% to about 95% LPVGt by weight.

7. The mixture of claim 1, comprising:
about 48.7% propanediol by weight;
about 46% VGt by weight;
about 2% *lobelia* by weight;
about 1% coltsfoot by weight;
about 1% *eucalyptus* by weight;
about 0.5% lungwort by weight;
about 0.5% oregano by weight; and
about 0.25% algae juice by weight.

8. A vaping cartridge, comprising:
a vape base, comprising:
- a mixture of propanediol and vegetal glycerin (VGt) derived from at least one of corn, coconut, soy, and bamboo, said mixture comprising between 91-99% of said base by weight; and
- a blend of botanicals including *lobelia* comprising between about 1-3% of said base by weight, coltsfoot comprising 0.5-2.0% of said base by weight, and algae juice comprising 0.1-2.5% of said base by weight.

9. The base of claim 8, wherein the propanediol comprises a laboratory produced propanediol (LPP).

10. The base of claim 8, wherein the VGt comprises a laboratory produced vegetal glycerin (LPVGt).

11. THe base of claim 8, wherein the blend of botanicals further comprises at least two botanicals selected from the group:
*eucalyptus;*
lungwort; and
oregano.

12. The base of claim 8, wherein said base comprises from about 5% to about 95% propanediol by weight.

13. The base of claim 8, wherein said base comprises from about 5% to aobut 95% VGt by weight.

14. The method of claim 11, comprising:
about 48.7% propanediol by weight;
about 46% VGt by weight;
about 2% *lobelia* by weight;
about 1% coltsfoot by weight;
about 1% *eucalyptus* by weight;
about 0.5% lungwort by weight;
about 0.5% oregano by weight; and
about 0.25% algae juice by weight.

15. The mixture of claim 1, wherein said one or more active ingredients comprises tetrahydrocannabinol.

16. The base of claim 8, furthere comprising tetrahydrocannabinol.

17. The mixture of claim 1, wherein said one or more active ingredients comprises a vitamin.

18. The base of claim 8, further comprising a vitamin.

* * * * *